Figure 1:
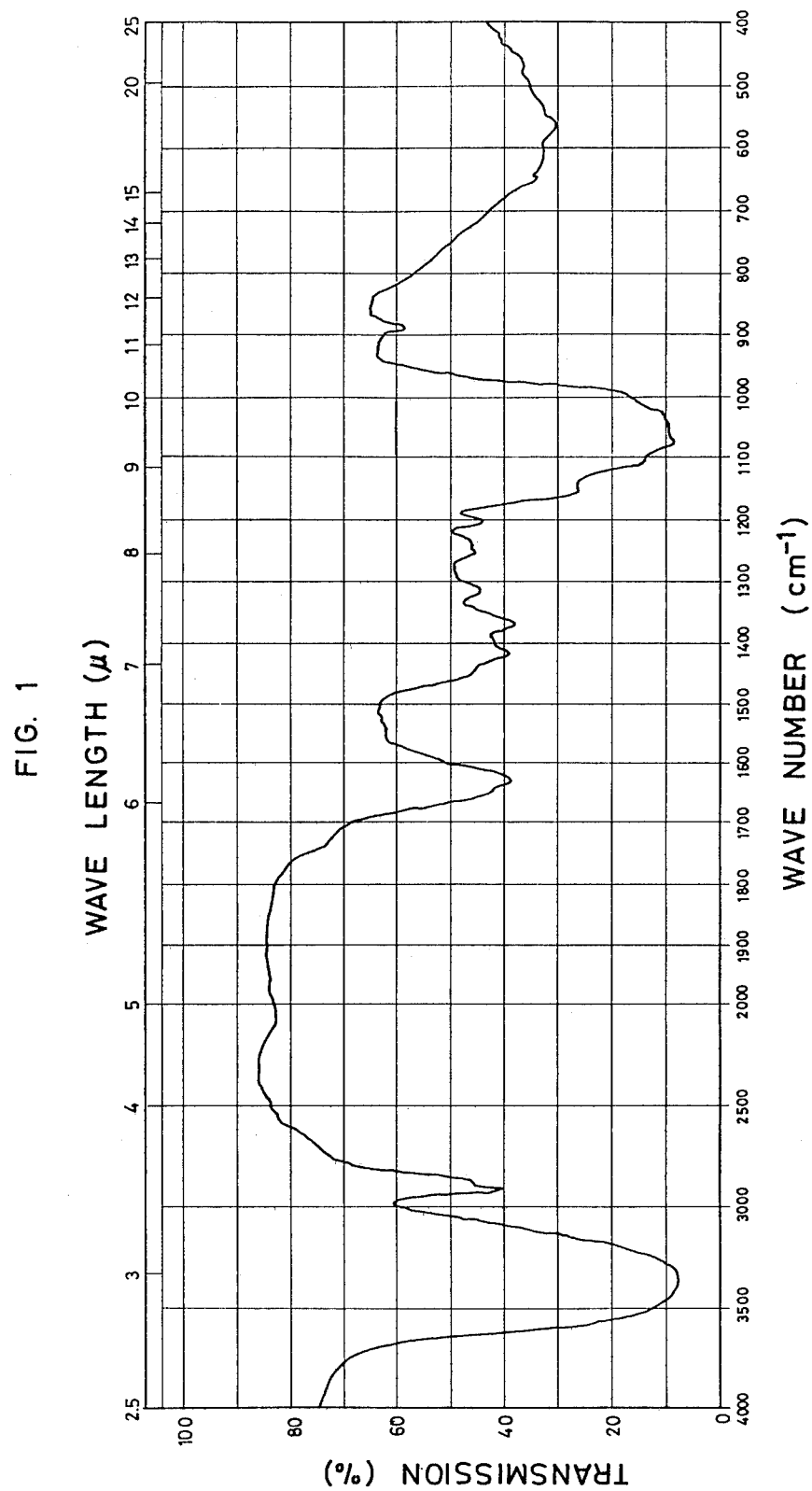

United States Patent [19]

Nakajima et al.

[11] 4,454,289
[45] Jun. 12, 1984

[54] POLYSACCHARIDES HAVING ANTICARCINOGENIC ACTIVITY AND METHOD FOR PRODUCING SAME

[75] Inventors: Kazuo Nakajima, Kyoto; Yoshiaki Hirata; Hiroyuki Uchida, both of Otsu; Tomoko Shiomi, Uji; Tsutomu Taniguchi, Kyoto; Akira Obayashi; Osamu Tanabe, both of Uji; Takuma Sasaki, Tokyo, all of Japan

[73] Assignee: Takara Shuzo Co., Ltd., Japan

[21] Appl. No.: 351,364

[22] Filed: Feb. 23, 1982

[30] Foreign Application Priority Data

Mar. 6, 1981 [JP] Japan .................................. 56-32797
Sep. 3, 1981 [JP] Japan ................................. 56-139039

[51] Int. Cl.³ ............................................. C08B 37/00
[52] U.S. Cl. ..................................... 536/1.1; 424/180
[58] Field of Search ......................................... 536/1.1

[56] References Cited

U.S. PATENT DOCUMENTS 4,225,673 9/1980 Sugiura et al. ...................... 536/1.1
4,237,266 12/1980 Sugiura et al. ...................... 536/1.1

OTHER PUBLICATIONS

Shvartsman et al., *Chemical Abstracts*, vol. 78, 1973, p. 1974, (1968 u).

*Primary Examiner*—Johnnie R. Brown
*Assistant Examiner*—Elli Peselev
*Attorney, Agent, or Firm*—Wenderoth, Lind & Ponack

[57] ABSTRACT

The invention relates to a high molecular weight $\beta$-1,3-glucan composed of repeated glucopyranose units, each unit being represented by the formula:

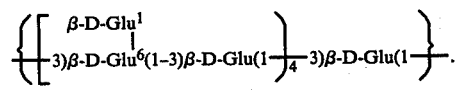

The $\beta$-1,3-glucan exhibits anticarcinogenic activity. A process for producing said glucan is also claimed.

5 Claims, 1 Drawing Figure

POLYSACCHARIDES HAVING ANTICARCINOGENIC ACTIVITY AND METHOD FOR PRODUCING SAME

This invention relates to polysaccharides having an anticarcinogenic activity and also to a process for producing the same.

More particularly this invention relates to new β-1,3-glucan having excellent anticarcinogenic activity and to a process for producing the same from an extract of mycelium and/or fruitbodies of a strain which is capable of producing an anticarcinogenic polysaccharide and which belongs to the genus Pseudoplectania, the tribe Sarcomateae, the family Sarcomataceae, the suborder Sarcoscyphineae, the order Pezizales, the class Discomycetes of the subdivision Ascomycotinia, or from a culture medium in which said strain has been incubated.

The β-1,3-glucan of this invention is a novel high molecular weight polysaccharide and is composed of the repeated glucopyranose units of the following formula (I):

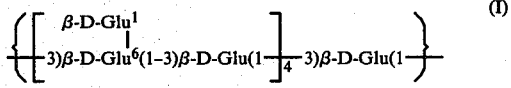

wherein "Glu" represents glucopyranose residue.

The β-1,3-glucan of this invention exhibits a strong anticarcinogenic activity against not only allogeneic tumors but also syngeneic tumors against which no such activity has been reported in connection with conventional β-1,3-glucans. Moreover this β-1,3-glucan also exhibits a strong anticarcinogenic activity against the allogeneic tumors "Sarcoma-180" in C3H/He mice, which are known to have a low immune response.

Heretofore there have been some investigations in which the chemical structure of the anticarcinogenic β-1,3-glucan was discussed. These are as follows:

(1) Schizophyllan:

The β-1,3-glucan which is produced from *Schizophyllum commune* (Fries.) (Journal of the Agricultural Chemical Society of Japan 44, 337–342, 1970; ibid 45, 162–168, 1971). Its chemical structure (as recurring unit) proposed therein is as follows:

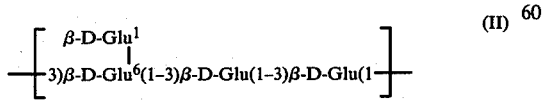

(2) The β-1,3-glucan which is produced from the genus Auricularia of class Basidiomycetes. (Japanese Patent Kokai No. 63012/1979). Its chemical structure (as recurring unit) proposed therein is as follows:

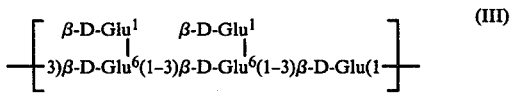

(3) Lentinan:

The β-1,3-glucan which is produced from *Lentinus edodes* (Berk.) Singer. (Nature 222, 687–688, 1969; Carbohydr. Research 47, 99–104, 1976; "Gan to Menekizokyo" ed. by Goro Chihara (published by Kodan-sha, Tokyo, Japan) 1980. Its chemical structure was proposed therein is as follows:

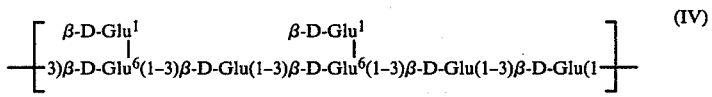

These known β-1,3-glucans and the β-1,3-glucan of this invention are common in having a β-(1,3) linked linear chain of D-glucopyranose units and β-(1,6) linked D-glucopyranose side chain(s). However, as apparent from the comparison of the formula (I) with the formulae (II), (III) and (IV), the β-1,3-glucan of this invention is different from the known β-1,3-glucans in the ratio of the number of β-1,3 linkages and the number of β-1,6 branch linkages. Thus the β-1,3-glucan of this invention is a new one different in chemical structure from the known β-1,3-glucans.

Furthermore, the β-1,3-glucan of this invention exhibits strong anticarcinogenic activity against not only allogeneic tumor but also syngeneic tumors. Hitherto there have not been reported β-1,3-glucan which exhibits strong anticarcinogenic activity against syngeneic tumors. Moreover the β-1,3-glucan of this invention also exhibits a strong anticarcinogenic activity against allogeneic tumors "Sarcoma-180" in C3H/He mice, which are known to have a low immune response. Therefore it is expected that the β-1,3-glucan of this invention is more effective than the known β-1,3-glucans as an immunotherapeutic drug of cancer.

The chemical structure and properties of the β-1,3-glucan of this invention are as follows:

(1) The chemical structure:

The chemical structure (as recurring unit) of this β-1,3-glucan is as shown by the formula (I), which has been confirmed by the following experiments;

(A) Treatment of this polysaccharide with exo-β-1,3-glucanase derived from the microorganism Basidiomycetes QM 806 yields D-glucose and gentiobiose and their molar ratio shows 1:0.8 by determination with Bio-gel P-2 gel-permeation chromatography.

(B) Methylation treatment by Hakomori's method of this polysaccharide and subsequent hydrolysis yields 2,3,4,6-tetra-O-methyl-D-glucose, 2,4,6-tri-O-methyl-D-glucose and 2,4-di-O-methyl-D-glucose identified by paper chromatography, gas chromatography, and mass-spectrometry and their molar ratio is 0.8:1:0.8 respectively.

(C) The periodate oxidation (by 0.05M periodate) of this polysaccharaide consumes 0.667 moles of periodate per anhydroglucose unit with concomitant liberation of 0.344 moles of formic acid.

(D) Treatment by Smith degradation of the above oxidized product yields glycerol and glucose in the molar ratio of 1:2.1.

(E) Treatment by mild hydrolysis (with 0.03M sulfuric acid) of the above oxidized and subsequent reduced product yields glycerol and water insoluble material, and methylation and subsequent hydrolization of this water insoluble material yields only 2,4,6-tri-O-methyl-D-glucose.

(F) Treatment of mild hydrolization (with 0.03M sulfuric acid) of this polysaccharide yields D-glucose and water insoluble material. On the other hand treatment of this water insoluble material with exo-β-1,3-glucanase described above yields only D-glucose.

From these results it is apparent that the polysaccharide of this invention is a β-1,3-glucan which has recurring glucopyranose units as shown by the formula

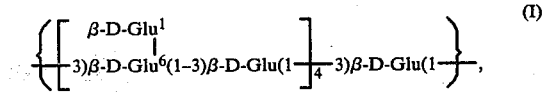
(I)

wherein there is a linear chain of β-(1,3) linked D-glucopyranose units with β-(1,6) linked and branched D-glucopyranose units (each branch being a single D-glucopyranose unit), in the ratio of 9:4.

(2) Elementary analysis: C: 43.88% H: 6.18%

(3) Molecular weight: More than $2.5 \times 10^5$ (gel-filtration method)

(4) Melting point: This substance is without a sharp melting point and carbonized upon strong heating.

(5) Specific rotation: $[\beta]_D^{25} = +35°$ (0.5N NaOH, C=0.5%)

(6) Intrinsic viscosity: $[\eta] = 20-25$

Intrinsic viscosity is defined by the following formula:

$$[\eta] = \lim_{c \to 0} \eta_{sp}/c$$

$\eta_{sp} = (\eta - \eta_o)/\eta_o = \eta/\eta_o - 1$

η: The viscosity of solution (0.1M NaCl 30° C.)
$\eta_o$: The viscosity of solvent.
c: g number of substance in 100 ml solution.

(7) UV spectrum: End absorption.

(8) Infra red spectrum: This substance shows a band at 890 cm$^{-1}$, indicating the presence of the β-glycosidic linkage.

(9) Solubility: This substance is soluble in water, 0.5N NaOH, and dimethyl sulfoxide, but insoluble in petroleum ether, ether, acetone, benzene, ethanol and methanol, etc.

(10) Color reaction: This substance shows a positive reaction to Molish reagent and Anthrone reagent, but shows negative reaction to Iodo-starch reagent, Bial reagent, Carbasol-H$_2$SO$_4$ reagent, ninhydrin reagent and Elson-Morgan reagent.

(11) pH of the solution: Neutral

(12) Appearance: White powder

(13) The sugar component: This substance is composed only of D-glucose. (confirmed by paper chromatography, thin-layer chromatography, gas-liquid chromatography and glucose oxidase method.)

As described above the β-1,3-glucan of this invention is a new β-1,3-glucan which has the structure of the formula (I) and physico-chemical properties of (2)-(13).

The β-1,3-glucan of this invention has an anti-carcinogenic activity. The anticarcinogenic activity of the new β-1,3-glucan (as obtained in Example 3) has been confirmed and determined by conventional methods unless otherwise mentioned in each experimental procedure, as follows.

EXPERIMENT (1)

The anticarcinogenic activity of the β-1,3-glucan of this invention against Sarcoma-180 in ICR mice has been determined. The results are shown in Table 1.

TABLE 1

| Dosage mg/kg/day | Inhibition ratio (%) | Complete regression |
|---|---|---|
| 0.2 | 85.0 | 3/5 |
| 2.0 | 100.0 | 5/5 |
| 20.0 | 83.3 | 3/5 |

Tumor cell:
  Sarcoma-180
Transplanted cell number:
  $4 \times 10^6$/mouse
Animal stock:
  ICR ♀
Treatment:
  Administered intraperitoneally starting one day after transplantation and subsequent administration was 5 times every other day. (control: saline)
Determination:
  Tumor weight of solid type was measured at 4 weeks after transplantation.

Inhibition ratio = $[(\overline{C} - \overline{T})/\overline{C}] \times 100$ $\overline{C}$: Average weight of tumors removed from the control group.
$\overline{T}$: Average weight of tumors removed from the β-1,3-glucan treated group.

EXPERIMENT (2)

The anticarcinogenic activity of the β-1,3-glucan of this invention against sarcoma-180 in C3H/He mice, Ehlrich-carcinoma in ICR mice and Meth-A fibrosarcoma in BALB/c mice has been determined.

The results are shown in Tables 2, 3 and 4.

TABLE 2

| Dosage mg/kg/day | Inhibition ratio (%) | Complete regression |
|---|---|---|
| 2.0 | 44.2 | 0/5 |
| 10.0 | 82.5 | 2/5 |
| 50.0 | 80.3 | 2/5 |

Tumor cell:
  Sarcoma-180
Transplanted cell number:
  $4 \times 10^6$/mouse
Animal stock:
  C3H/He ♀
Treatment:
  Administered intraperitoneally starting one day after transplantation and subsequent administration was 10 times every other day. (control: saline)
Determination:
  Tumor weight of solid type was measured at 5 weeks after transplantation.

Inhibition ratio = $[(\overline{C} - \overline{T})/\overline{C}] \times 100$ $\overline{C}$: Average weight of tumors removed from the control group.

T̄: Average weight of tumors removed from the β-1,3-glucan treated group.

TABLE 3

| Dosage mg/kg/day | Inhibition ratio (%) | Complete regression |
|---|---|---|
| 0.06 | 80.3 | 1/5 |
| 0.60 | 100.0 | 5/5 |
| 6.00 | 92.4 | 4/5 |

Tumor cell:
  Ehlrich carcinoma
Transplanted cell number:
  $4 \times 10^6$/mouse
Animal stock:
  ICR ♀
Treatment:
  Administered intraperitoneally starting one day after transplantation and subsequent administration was 8 times every other day. (control: saline)
Determination:
  Tumor weight of solid type was measured at 5 weeks after transplantation.

Inhibition ratio = $[(\bar{C}-\bar{T})/\bar{C}] \times 100$

C̄: Average weight of tumors removed from the control group.
T̄: Average weight of tumors removed from the β-1,3-glucan treated group.

TABLE 4

| Dosage mg/kg/day | Inhibition ratio (%) | Complete regression |
|---|---|---|
| 0.2 | 84.2 | 3/5 |
| 2.0 | 100.0 | 5/5 |
| 20.0 | 53.8 | 2/5 |

Tumor cell:
  Meth-A fibrosarcoma
Transplanted cell number:
  $1 \times 10^5$/mouse
Animal stock:
  BALB/c ♀
Treatment:
  Administered intratumorally starting one day after transplantation and subsequent administration was 10 times every other day. (control: saline)
Determination:
  Tumor weight of solid type was measured at 5 weeks after transplantation.

Inhibition ratio = $[(\bar{C}-\bar{T})/\bar{C}] \times 100$

C̄: Average weight of tumors removed from the control group.
T̄: Average weight of tumors removed from the β-1,3-glucan treated group.

EXPERIMENT (3)

The anticarcinogenic activity of the β-1,3-glucan of this invention against Ehlrich ascites tumors in ICR mice has been determined.
The result is shown in Table 5.

TABLE 5

| Dosage mg/kg/day | Average survival (days) | Survival numbers of group |
|---|---|---|
| Control | 13.3 | 0/5 |
| 0.24 | 15.2 | 0/5 |
| 1.20 | 23.2 | 0/5 |
| 6.10 | >31.4 | 3/5 |

Tumor cell:
  Ehlrich ascites tumor
Transplanted cell number:
  $5 \times 10^5$/mouse
Animal stock:
  ICR ♀
Treatment:
  Administered intraperitoneally starting one day after transplantation and subsequent administration was 10 times every day. (control: saline)
Determination:
  The numbers of survival mouse and the survival days of each group were measured at 7 weeks after transplantation.

As shown in the above Experiments (1)–(3) the β-1,3-glucan of this invention exhibits strong anticarcinogenic activity against not only the allogeneic tumor "Sarcoma-180" in ICR mice but also the syngeneic tumor "Meth-A fibrosarcoma" in BALB/c mice. It should be pointed out that hitherto there has not been reported such β-1,3-glucan which exhibits strong anticarcinogenic activity against syngeneic tumor "Meth-A fibrosarcoma" in BALB/c mice. Moreover the β-1,3-glucan of this invention also exhibits strong anticarcinogenic activity against allogeneic tumor "Sarcoma-180" in C3H/He mice, which are known to have a low immune response.

The β-1,3-glucan of this invention exhibits neither direct cytotoxicity in vitro nor side effects commonly seen in connection with the use of conventional agents such as decrease in number of leucocyte, anemia of liver and other organs, atorophy of spleen, loss of body weight and loss of appetite. The acute toxicity (LD$_{50}$) of this β-1,3-glucan in mice is more than 1000 mg/kg when intraperitoneally injected.

The new polysaccharide or β-1,3-glucan of this invention can be obtained from an extract of mycelium and/or fruitbodies of a strain which is capable of producing an anticarcinogenic β-1,3-glucan and which belongs to the genus Pseudoplectania, the tribe Sarcomateae, the family Sarcomataceae, the suborder Sarcosyphineae, the order Pezizales, the class Discomycetes of the subdivision Ascomycotinia, or from a culture medium in which said strain has been incubated.

According to this invention there can be used any strain of species belong to the genus described above and which is capable of producing an anticarcinogenic polysaccharide.

However in the embodiments of this invention to be explained hereinafter there was used a strain of *Pseudoplectania nigrella* (Pers.) Fuckel K-1426 which was obtained by the cultivation of a fruitbody (tissue) of a fungus species collected in a suburb of Sapporo in Hokkaido prefecture, Japan in the May of 1969.

The identification of this species was made by the following book; "Transactions of The Mycological Society of Japan" 21, 149–179, 1980.

The characteristics of this strain are as follows.

This organism was collected in the moss of a coniferous forest and its body has the typical characteristics of the genus Pseudoplectania. Thus it is black-colored and its cap is about 1 cm in diameter and has no stem. The outside of this fruitbody is covered with velvet-like hairs and its ectel excipulum is composed of t.angularis and 100–150 μm in depth. The medullary tissue is composed of t.intricata and is 250–400 μm in depth. There are dark-brown, long, branched hairs in the outer side of ectel excipulum which is intertwined together and is about 150 μm in depth. The ascus is composed of sclerenchyma and is cylindrical in shape and 220–300×12–15 μm. The ascospore is nearly global in shape and is 11–14 μm in diameter. The mycelium is filamentous and 2–3 μm in diameter. The upper side of its filament is slightly expanded.

From these characteristics and by referring to the above cited book this strain was identified as *Pseudoplectania nigrella* (Pers.) Fuckel. This strain was deposited at Fermentation Research Institute, Agency of Industrial Science and Technology, Japan under FERM-P 5803 and also at American Type Culture Collection under ATCC 20609.

According to this invention there can be used any strain of species belong to the genus Pseudoplectania of the class Discomycetes and which is capable of producing an anticarcinogenic polysaccharide.

The polysaccharide of this invention can be obtained from an extract of mycelium and/or fruitbodies of a strain which belongs to the genus Pseudoplectania of the class Discomycetes or from a culture medium in which said strain has been incubated.

However, it is not easy to collect such fruitbodies in a sufficiently large amount in natural surroundings. Therefore, it is advantageous to use the cultured mycelium. The mycelium to be used in this invention may be obtained by a conventional cultivation method such as solid culture or liquid culture. In solid culture, for example, agar, gelatin, starch, saw-dust, malt, rice-bran, soybean meal and other conventional solid culture medium or a combination thereof may be used. In liquid culture there may be used a liquid culture medium containing various nutrients which are well known in the art of cultivation of microorganisms. Thus the liquid culture medium may contain a carbon source such as glucose, maltose, lactose, sucrose, starch, oil, molasses, etc., a nitrogen source (organic and inorganic nitrogen source material) such as peptone, yeast extract, corn steep liquor, ammonium salts, urea, etc., and one or more of organic and inorganic salts such as phosphates, magnesium salts, etc. If desired, other materials necessary for the growth such as vitamins may also be added.

These materials for solid and liquid media are well known per se in the art of cultivation of fungus, and no further detailed explanation would be required therefor.

The liquid culture may be conducted in any conventional manner such as static culture, shaking culture or submerged culture. From an economical and handling point of view, liquid culture with aeration and stirring is more advantageous than solid culture.

In conducting the liquid culture the following conditions may be used:

Initial pH: 2–9
Incubation temp.: 15°–35° C.
Incubation period: 3–30 days

In the case of submerged culture the medium is subjected to aeration at a rate of 0.1–2.0 L/L/min. with stirring at a rate of 30–500 r.p.m.

The mycelium grown by the solid or liquid culture is collected in a conventional manner and used as the starting material of this invention.

For example, in the case of liquid culture, the mycelium may be collected by subjecting the resulting liquid culture medium to a conventional separating procedure such as centrifugation, filtration, etc. The filtrate obtained by this separation procedure is referred to as filtered broth, which may also be used as the starting material of this invention.

According to this invention, the fruitbodies and/or mycelium collected in the above mentioned manner is subjected to extraction with an aqueous solvent. In this case fruitbodies and/or mycelium as such may be directly subjected to the extraction. If desired, prior to such extraction, the fruitbodies and/or mycelium may be subjected to a pretreatment such as washing with water, air drying, crushing (pulverization) or extraction with a non-polar solvent.

The aqueous solvent to be used for the extraction is water or a mixture of water and at least one water soluble material such as acid, base, salt, or organic solvent.

In conducting the extraction the pretreated or non-pretreated fruitbodies or mycelium is mixed with the aqueous solvent. The temperature of solvent is not critical if maintained not higher than 120° C. Preferably temperatures may be chosen from an economic viewpoint. The extraction is conducted for a period of time sufficient to effect the desired extraction. Generally, at a higher temperature the extraction time may be shorter. Within the above indicated preferred temperature range, the extraction is carried out preferably for a period of time from 30 minutes to 10 hours. The extraction is carried out preferably under agitation in a vessel which may be made of glass, glass-lined, enameled or stainless steel. The amount of solvent may also vary over a wide range but generally 10–100 times the weight (on dry basis) of the fruitbodies and/or mycelium. The use of pulverlized fruitbodies or mycelium is preferable for the extraction. After the extraction the mycelium or fruitbodies and other solid matter are removed from the liquid extract by any convenient means such as filtration or centrifugation. The liquid extract is concentrated, for example, by vacuum evaporation or the like for further treatment. Generally the aqueous extract is concentrated to ⅓–1/10 of initial volume.

The extract obtained as described above is then subjected to purification to be explained below, resulting in the precipitation and recovery of the intended polysaccharide. The term "liquid extract" as used herein means a filtrate or centrifugate resulting from the removal of the mycelium and/or fruitbodies and other solid matters from the extract.

The filtered broth may also and preferably be used for the purification to be explained below, resulting in the precipitation and recovery of the intended polysaccharide. The term "filtered broth" as used herein means a filtrate containing the active ingredient, i.e. polysaccharide and obtained by the removal of mycelium and other solid matters from the cultured broth, i.e. culture medium in which the strain has been incubated by liquid culture in the manner as explained before. The filtered broth is concentrated, for example, by vacuum evaporation or the like for further treatment. Generally the filtered broth is concentrated to ⅓–1/10 of the initial volume. The concentrated filtered broth is then subjected to purification.

The liquid extract and the filtered broth may be subjected to purification separately, or the liquid extract and filtered broth may be combined together so that the mixture is subjected to purification.

Purification may be conducted in any of the following procedures.

(A) Precipitation of the desired substance by the addition of a highly polar organic solvent (such as lower alcohols and ketones, e.g. methanol, ethanol, propanol, butanol, acetone, etc.) or salting out (by the addition of water-soluble inorganic salts such as ammonium sulfate, sodium chloride, potassium chloride, etc.).

(B) Removing acids, ions and low molecular weight substances by any of dialysis, Reverse osmosis, gel filtration (by the use of dextran or polyacrylamide gel such as Sephadex, Bio-Gel, etc.), ion exchange resin treatment (by the use, for example, of various commercial anion and cation exchange resins such as Amberlite, Dowex, Duolite, etc.), ultrafiltration and a combination thereof, to produce a substantially pure solution from which the desired active substance is recovered.

(C) Treatment for removal of free proteins, such as Sevag method, trifluorotrichloromethane method, protease treatment, etc.

These procedure are well known per se in the art. If desired two or more of them may be combined. Generally, however, the liquid extract or filtered broth, after concentration, is subjected to a procedure selected from ion-exchange resin treatment, dialysis, reverse osmosis, gel filtration, ultrafiltration and a combination thereof to effect decoloration, deacidification, and removal of low molecular weight substances. From such purified solution the desired active substance may be removed by a proper procedure such as freeze drying. If desired the above mentioned procedure(s) may be repeated to obtain a desired extent of purification.

The substance thus obtained has following characteristics explained hereinbefore.

The invention will be further explained in the following Examples with reference partly to FIG. 1 which is an infrared spectrum of the polysaccharide according to this invention.

EXAMPLE 1

A strain (FERM-P 5803, ATCC 20609) of *Pseudoplectania nigrella* (Pers.) Fuckel K-1426 was incubated in the following culture medium:

| | |
|---|---|
| Glucose | 20 g. |
| Corn steep liquor | 5 g. |
| Soybean meal | 1 g. |
| Yeast extract | 1 g. |
| Potassium phosphate (primary) | 1 g. |
| Magnesium sulphate (7H$_2$O) | 0.5 g. |
| Water | 1 liter |
| Initial pH | 5.6 |

The incubation was conducted by charging 100 ml of the above culture medium to each of 500 ml Erlenmeyer flasks. The flasks were stopped with cotton, sterilized for 20 minutes at 120° C. After cooling it was inoculated in a conventional manner with said strain which had been cultured separately in a slant culture medium containing 2% glucose, 0.5% Ebios and 1.5% agar. After 10 days incubation at 27° C., the contents of flasks were used for the subsequent incubation. Twenty liters of the liquid culture medium described above in 30 liters stainless steel jar fermenter were sterilized at 120° C. for 20 minutes and cooled. Then, the content of the flasks obtained above was inoculated in the culture medium in said jar fermenter. The medium was subjected to aerobic incubation with stirring (200 r.p.m.) for 12 days at 27° C., and with an aeration rate of 0.5 liter/liter/minute. The cultured broth thus obtained was filtered to obtain 130 g. of mycelium (dry) and 17 liters of filtered broth. The term "filtered broth" as herein means a filtrate containing the active ingredient, i.e. polysaccharide and obtained by the removal of mycelium and other solid matters from the cultured broth, i.e. culture medium in which the strain has been incubated by liquid culture in the manner as explained before.

EXAMPLE 2

The mycelium (130 g.) obtained in Example 1 was washed with one liter of water and the washing liquid was combined with the filtered broth. The washed mycelium was mixed with 15 liters of water and the mixture was heated at 120° C. for 30 minutes in a closed vessel. Then the mixture was allowed to cool to room temperature and then filtered. This procedure was repeated twice and obtained 43 liters of the extract. The extract obtained above was concentrated to 1/10 of initial volume. The concentrated extract was added with an equal volume of ethanol to precipitate the polysaccharide, which was separate. Then, this precipitate was dissolved in water and dialysed. The dialysate was treated with DEAE-sephadex ion-exchange chromatography and the non-absorbent fraction of DEAE-sephadex ion-exchange chromatography was also treated with SP-sephadex ion-exchange chromatography. The non-adsorbent fraction of SP-sephadex ion-exchange chromatography obtained above was dialyzed again and then freeze-dried to yield 8.6 g. of white powdery substance. This substance was identified as the β-1,3-glucan having the repeated units of the formula (I) by the Experiments (A)–(E) mentioned before. The average molecular weight of this β-1,3-glucan was about $1 \times 10^6$ (gel-filtration method).

EXAMPLE 3

The 17 liters of the filtered broth obtained in Example 1 was treated in the same manner as in Example 2 to yield 13.2 g. of white powdery substance. This substance was identified as the β-1,3-glucan having the repeated units of the formula (I) by the Experiments (A)–(E) mentioned before. The average molecular weight of this β-1,3-glucan was about $1 \times 10^6$ (gel-filtration method).

The infra red spectrum of this substance is shown in FIG. 1.

What we claim is:

1. A β-1,3-glucan composed of repeated glucopyranose units, each unit being represented by the formula:

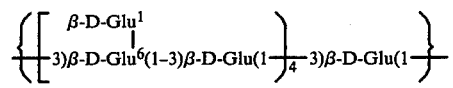

having an intrinsic viscosity $(\eta) = 20$–$25$, a molecular weight of more than $2.5 \times 10^5$ by the gel filtration method and an anticarcinogenic activity against Sarcoma-180, Ehrlich carcinoma, Ehrlich ascites tumor and Meth-A (fibrosarcoma), said β-1,3-glucan being produced by a process which consists essentially of forming a filtered broth from a culture medium or liquid extract of fruitbodies or mycelium of a strain which is capable of producing the β-1,3-glucan and belongs to the genus Pseudoplectania of the class Discomycetes, and recovering the β-1,3-glucan from the filtered broth or liquid extract in a purified form.

2. The high molecular weight β-1,3-glucan according to claim 1, wherein said β-1,3-glucan is as isolated from an extract of mycelium and/or fruitbodies of a strain which is capable of producing an anticarcinogenic β-1,3-glucan and which belongs to the genus Pseudoplectania of class Discomycetes or from a culture medium in which said strain has been incubated.

3. The high molecular weight β-1,3-glucan according to claim 2, wherein said strain is *Pseudoplectania nigrella* (Pers.) Fuckel K-1426 (FERM-P 5803, ATCC 20609).

4. A process for producing a high molecular weight β-1,3-glucan composed of repeated glucopyranose units, each unit being represented by the formula:

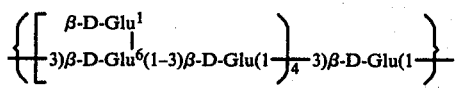

having an intrinsic viscosity $(\eta)=20-25$, a molecular weight of more than $2.5\times 10^5$ by the gel filtration method and an anticarcinogenic activity against Sarcoma-180, Ehrlich carcinoma, Ehrlich ascites tumor and Meth-A fibrosarcoma, which consists essentially of forming a filtered broth from a culture medium or liquid extract of fruitbodies or mycelium or a strain which is capable of producing the β-1,3-glucan and belongs to the genus Pseudoplectania of the class Discomycetes, and recoverying the β-1,3-glucan from the filtered broth or liquid extract in a purified form.

5. The process according to claim 4, wherein the strain is *Pseudoplectania nigrella* (Pers.) Fuckel K-1426 (FERM-P 5803, ATCC 20609).

* * * * *